(12) United States Patent
Robinson et al.

(10) Patent No.: US 7,048,736 B2
(45) Date of Patent: May 23, 2006

(54) DEVICE FOR FIXATION OF SPINOUS PROCESSES

(75) Inventors: James C. Robinson, Atlanta, GA (US); Paul Wisnewski, Germantown, TN (US); Jonathan Blackwell, Cordova, TN (US); W. Barry Null, Olive Branch, MI (US)

(73) Assignee: SDGI Holdings, Inc., Wilmington, DE (US)

( * ) Notice: Subject to any disclaimer, the term of this patent is extended or adjusted under 35 U.S.C. 154(b) by 674 days.

(21) Appl. No.: 10/147,554

(22) Filed: May 17, 2002

(65) Prior Publication Data

US 2003/0216736 A1    Nov. 20, 2003

(51) Int. Cl.
*A61B 17/70* (2006.01)

(52) U.S. Cl. .......................................... 606/61
(58) Field of Classification Search ............... 606/61, 606/69, 70, 71
See application file for complete search history.

(56) References Cited

U.S. PATENT DOCUMENTS

| | | |
|---|---|---|
| 2,774,350 A | 12/1956 | Cleveland, Jr. |
| 3,426,364 A | 2/1969 | Lumb |
| 3,648,691 A | 3/1972 | Lumb et al. |
| 3,693,616 A | 9/1972 | Roaf et al. |
| 4,554,914 A | 11/1985 | Kapp et al. |
| 5,011,484 A | 4/1991 | Breard |
| 5,496,318 A | 3/1996 | Howland et al. |
| 5,609,634 A | 3/1997 | Voydeville |
| 5,645,599 A | 7/1997 | Samani |
| 5,725,582 A | 3/1998 | Bevan et al. |
| 5,836,948 A | 11/1998 | Zucherman et al. |
| 5,860,977 A | 1/1999 | Zucherman et al. |
| 6,048,342 A | 4/2000 | Zucherman et al. |

(Continued)

FOREIGN PATENT DOCUMENTS

GB    780652    8/1957

OTHER PUBLICATIONS

"Posterior Spinal Instrumentation for Thoracolumbar Tumor and Trauma Reconstruction", Glenn M. Amundson and Steven R. Garfin; *Seminars in Spine Surgery*, vol. 9, No. 3 (Sep), 1997:pp. 260-277.

(Continued)

*Primary Examiner*—David O. Reip
(74) *Attorney, Agent, or Firm*—Krieg DeVault LLP

(57) ABSTRACT

A fixation device for use in association with ALIF procedures includes a couple of spaced plates having integral spikes on facing surfaces thereof for pressing into spinal processes of adjacent vertebrae. One of the plates has a spherical socket which captures a spherical head end of a post whose other end is received through an aperture in the other plate. The socket mounting is arranged to enable the post to pivot therein for at least two degrees of freedom to a limited extent, enabling angulation between the two plates so as to accommodate the different thicknesses and orientations of the spinal processes on adjacent vertebrae. The reception of the post in the second plate enables adjustment of spacing between the plates to accommodate effective installation of the assembly on the spinal processes by a compression instrument, and permanent reliable maintenance of that spacing following removal of the compression instrument. The cross-sectional configuration of the post and a receiver aperture in the plate inhibits rotation of the plate relative to the post about the post axis, and a set screw in the apertured plate engages a flat on the post fixing the interplate space as adjusted.

34 Claims, 6 Drawing Sheets

U.S. PATENT DOCUMENTS

| | | | |
|---|---|---|---|
| 6,068,630 | A | 5/2000 | Zucherman et al. |
| 6,312,431 | B1 | 11/2001 | Asfora |
| 6,364,883 | B1 | 4/2002 | Santilli |
| 6,451,019 | B1 | 9/2002 | Zucherman et al. |
| 6,500,178 | B1 | 12/2002 | Zucherman et al. |
| 6,626,944 | B1 | 9/2003 | Taylor |
| 6,695,842 | B1 | 2/2004 | Zucherman et al. |
| 6,733,534 | B1 | 5/2004 | Sherman |
| 2002/0143331 | A1 | 10/2002 | Zucherman et al. |
| 2003/0040746 | A1* | 2/2003 | Mitchell et al. ............ 606/61 |
| 2003/0065330 | A1 | 4/2003 | Zucherman et al. |
| 2004/0106995 | A1 | 6/2004 | Le Couedic et al. |
| 2004/0181282 | A1 | 9/2004 | Zucherman et al. |

OTHER PUBLICATIONS

"Reduction and Fixation of Late Diagnosed Lower Cervical Spine Dislocations Using the Daab Plate A Report of Two Cases", O. Korkala and J. Kytomaa; *Archives of Orthopaedic and Traumatic Surgery*, (1984), vol. 103:pp. 353-355.

"Posterior spinal fusion using internal fixation with the Daab plate", Ole Bostman, Pertti Myllynen and Erik B. Riska; *Acta Orthop Scand*, 55, 310-314 (1984).

"The Value of the Wilson Plate in Spinal Fusion", Milton C. Cobey, M.D., F.A.C.S., *Clinical Orthopaedics and Related Research*, No. 76:pp. 138-140, May, 1971.

\* cited by examiner

DEVICE FOR FIXATION OF SPINOUS PROCESSES

BACKGROUND OF THE INVENTION

1. Field of the Invention

This invention relates generally to spinal surgery, and more particularly to devices for stabilization of the spine in association with placement of an inter-body construct for interbody fusion or the like.

2. Description of the Prior Art

Varieties of inter-body fusion devices are widely used following partial or total discectomies, for stabilization of the spine at the site. Some stabilization devices are anchored to the pedicles. With several systems, the use of the pedicles requires screws or other anchorage devices that occupy significant space and involve muscle dissection and associated work time for implantation. We believe that such elaborate apparatus and procedures are unnecessary in many instances.

Breard et al. U.S. Pat. No. 5,011,484 issued Apr. 30, 1991 discloses an artificial ligament used with an elongate insert. A couple of types of systems, one including rods and another including inextensible strips or inextensible bands, are mentioned as background in U.S. Pat. No. 5,725,582 issued Mar. 10, 1998 to Bevan et al. One such mentioned system is to loop inextensible flexible members directly around spinous processes. The Bevan et al. patent discloses a proposed simplification of the loop procedure, by simply winding the band around spinous processes of adjacent vertebrae as in FIGS. 1 and 2 of that patent, and then tensioning and crimping them. Bevan et al. shows other versions which involve pedicle screws and hooks. The Howland et al. U.S. Pat. No. 5,496,318 uses an arrangement mounted on spinous processes and has a retaining belt 124. Lumb et al. U.S. Pat. No. 3,648,691 uses flexible multi-apertured straps 28 clamped on opposite sides of spinous processes. Vinylidene flouride is given as an example of the strap material and is said to be preferred over machined metal straps. The Kapp et al. U.S. Pat. No. 4,554,914 discloses a pair of elongate plates 28 and 30 clamped onto the spinal processes by bolts through holes drilled in the spinal processes. The Samani U.S. Pat. No. 5,645,599 employs a U-shaped body preferably made of titanium forged in one piece and having upper and lower generally U-shaped brackets with holes therein. The brackets are receivable on spinous processes of adjacent vertebrae and have holes therein to receive bone screws or spikes engaged in the spinous processes and crimped in the holes to anchor the implant thereon.

In our view, and to various degrees, these systems involve one or more of a variety of shortcomings such as size, the necessity of large incisions, difficult manipulation, difficult or excessive drilling or sawing of bone, and permanence and reliability of fixation in association with anterior lumbar interbody fusion (ALIF) procedures. The present invention is directed to overcoming one or more shortcomings encountered with current fixation devices and systems following such procedures.

SUMMARY OF THE INVENTION

Described briefly, according to a typical embodiment of the present invention, a fixation device for use in association with ALIF procedures includes a couple of spaced plates having integral spikes on facing surfaces thereof for pressing into spinal processes of adjacent vertebrae. One of the plates has a socket which captures one end of a post which is received through an aperture in the other plate. The socket mounting is arranged to enable the post to pivot therein for at least two degrees of freedom to a limited extent enabling angulation between the two plates so as to accommodate the different thicknesses and orientations of the spinal processes on adjacent vertebrae. The reception of the post in the second plate enables adjustment of spacing between the plates to accommodate effective installation of the assembly on the spinal processes by a compression instrument, and permanent reliable maintenance of that spacing following removal of the compression instrument. The cross-sectional configuration of the post and a receiver aperture in the plate inhibits rotation of the plate relative to the post about the post axis.

DESCRIPTION OF THE PREFERRED EMBODIMENT

Figure 1:
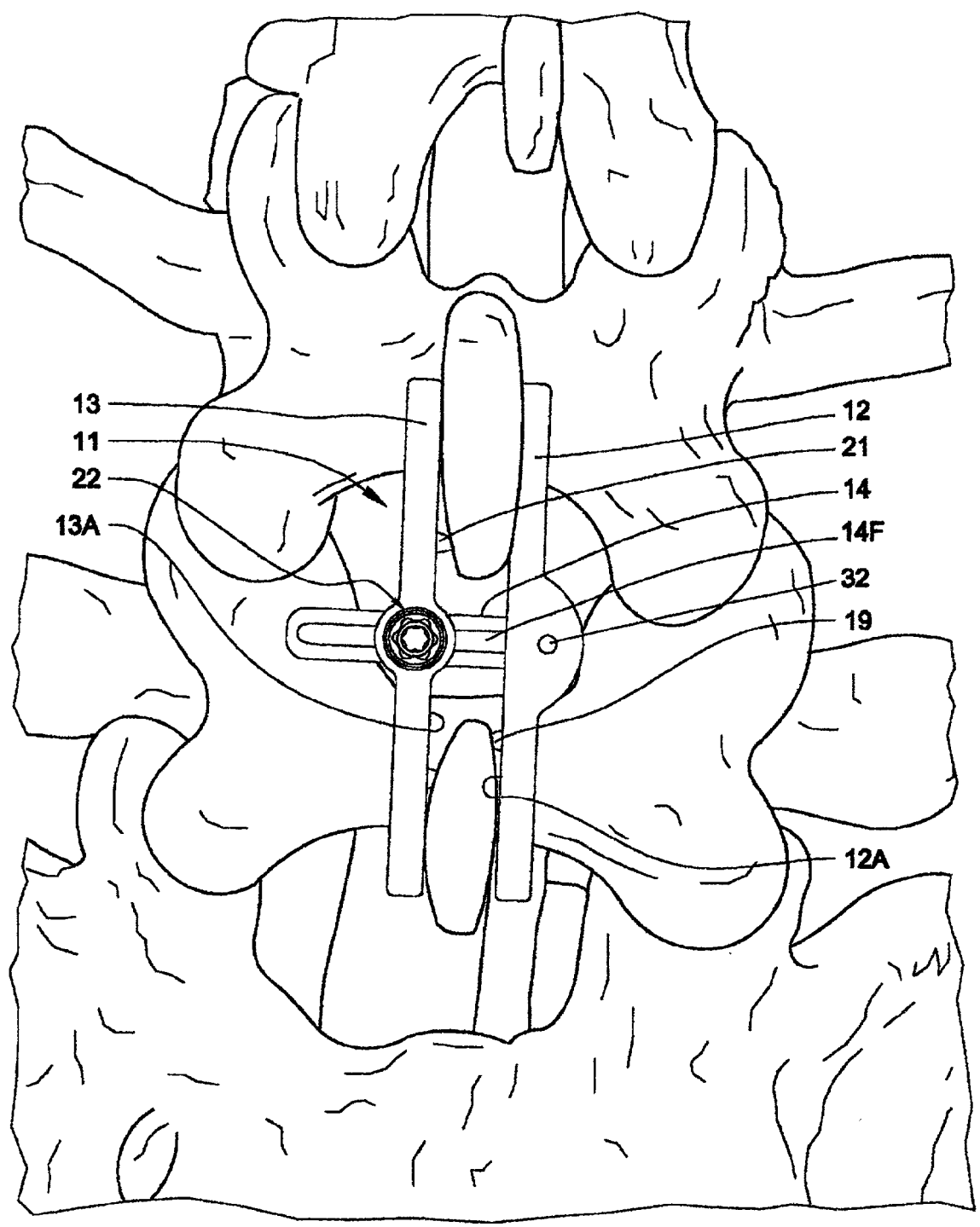
FIG. 1 is a posterior view of a portion of the spine with the device of the present invention fixed in place following anterior lumbar interbody fusion procedure.
Figure 2:
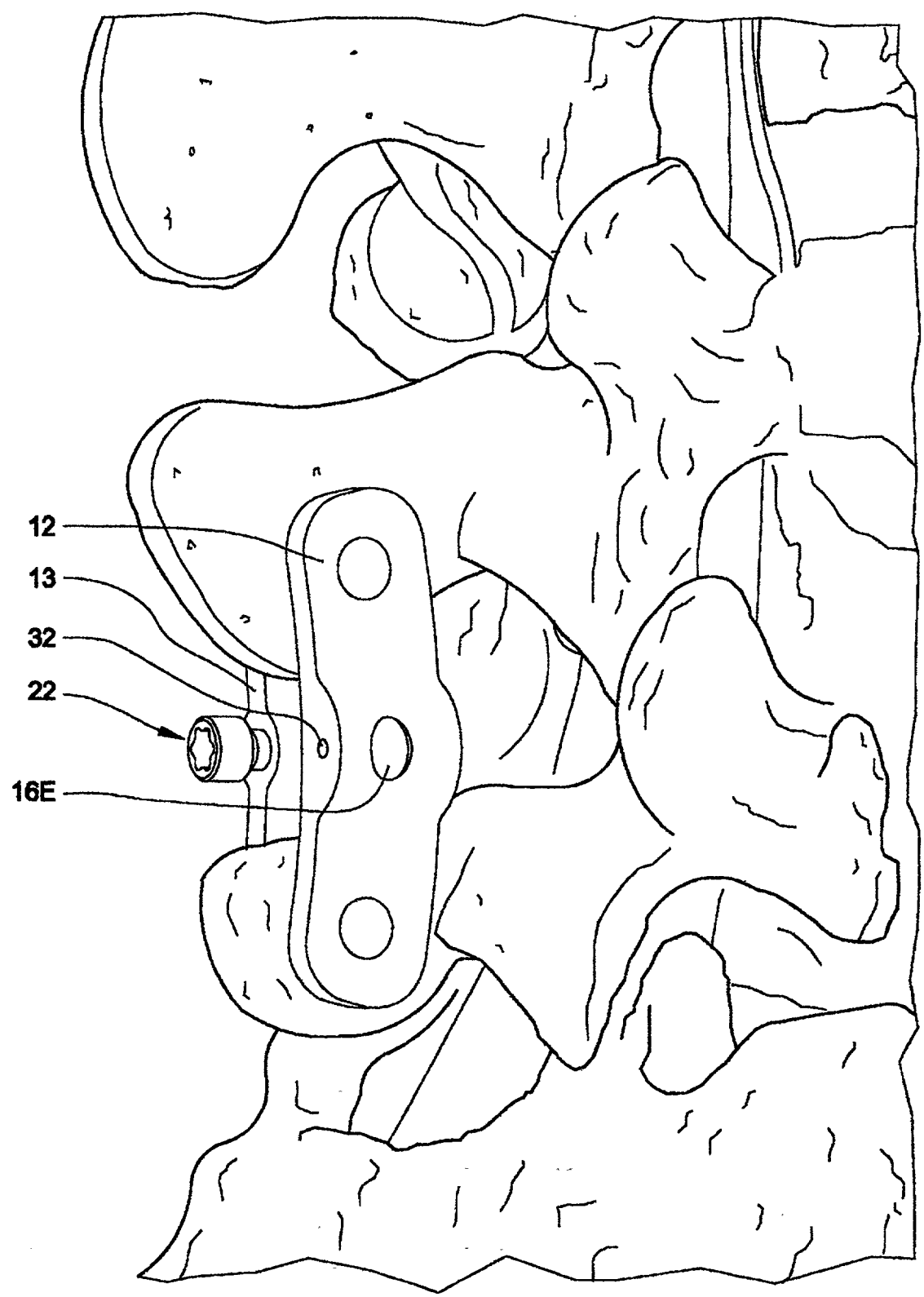
FIG. 2 is a lateral view of the instrumentation of FIG. 1.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 3:
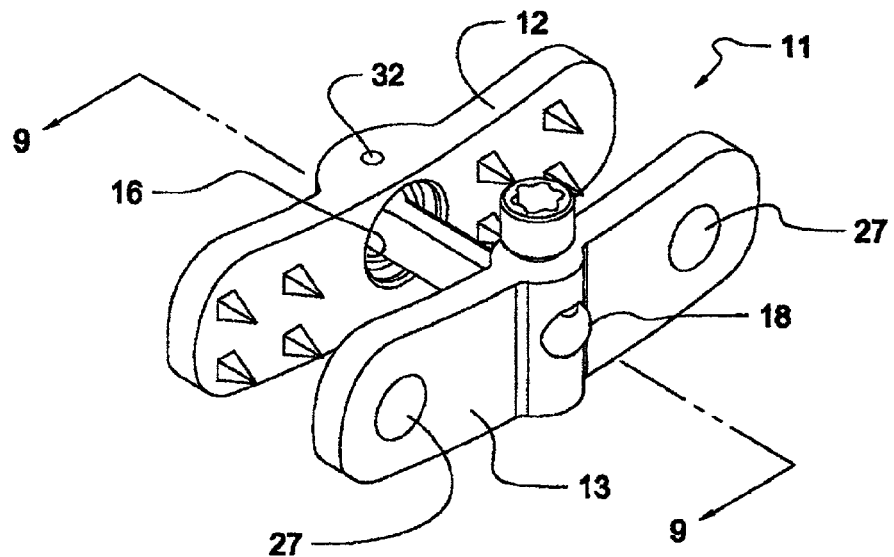
FIG. 3 is a perspective view of the device itself prior to installation.
Figure 9:
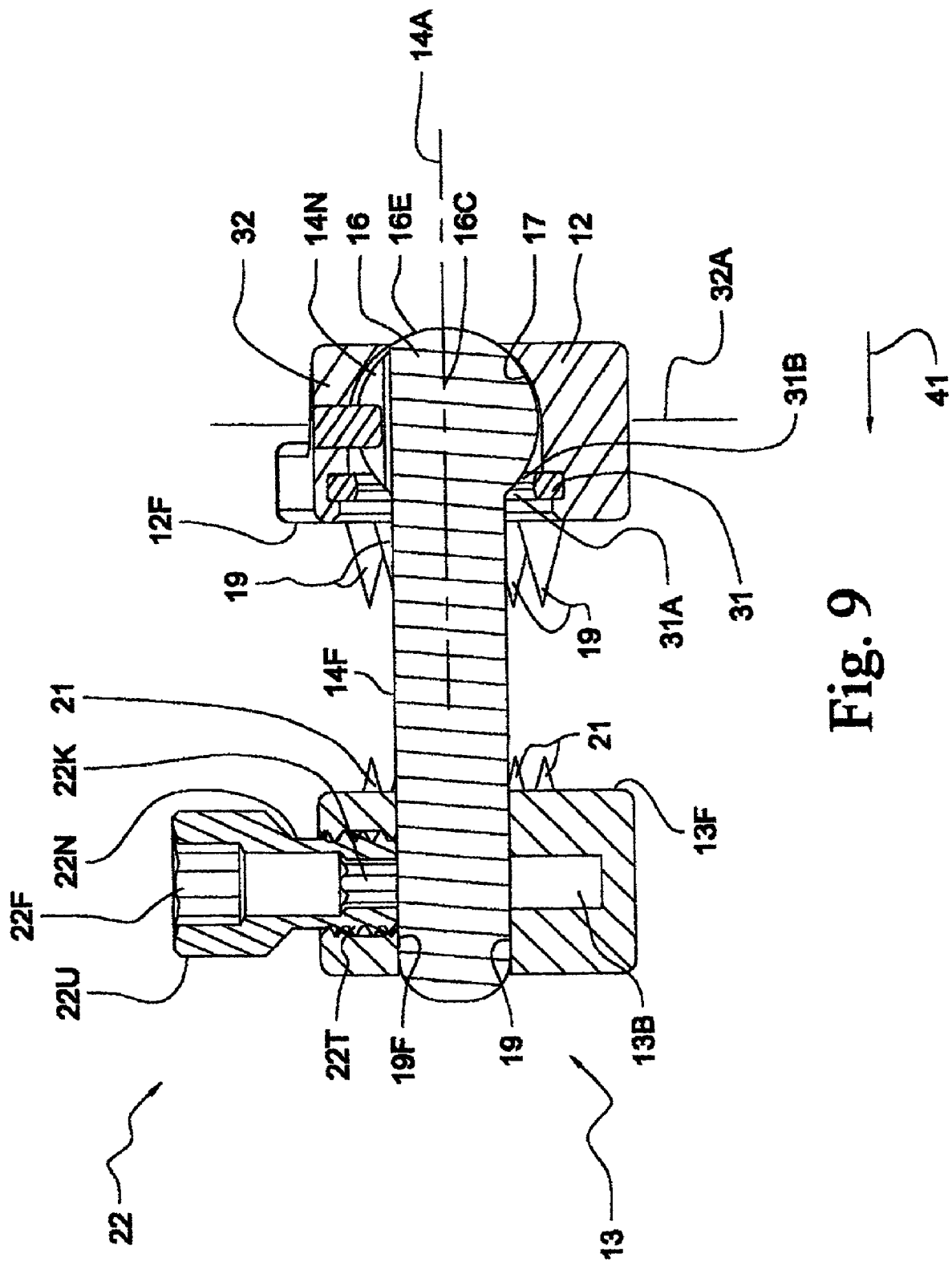
FIG. 9 is a section taken through the assembly of FIG. 3 on the axis of the cross-post and viewed in a plane containing the axis of the cross-post and set screw and viewed in the direction of the arrows 9—9.
Figure 10:
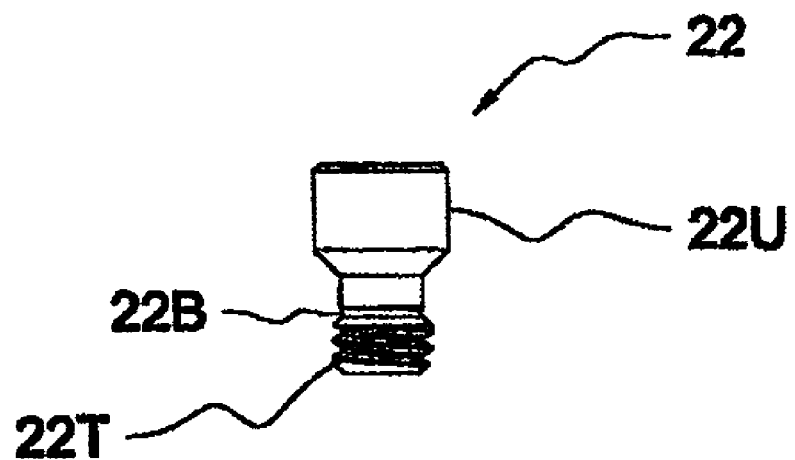
FIG. 10 is an enlarged elevational view of the breakoff set screw.

Referring now to the drawings in detail, particularly FIGS. 3 and 9, the device 11 according to the illustrated embodiment of the present invention, is clamped to the spinal processes of the L4 and L5 vertebrae. The device comprises a head plate 12, a locking plate 13, and a cross-post 14 having a head 16 received in a socket 17 in the head plate, and a distal end 18 received through an aperture 19 in the locking plate. The inboard or inside surface 12A of plate 12 facing the inside or inboard face 13A of plate 13, has a plurality of spikes 19 facing similar spikes 21 on the inside face 13A of plate 13. These spikes are embedded in the spinal processes when the device is compressed in place and so clamps the adjacent vertebrae.

The cross-post has a cylindrical cross-sectional shape but with a flat surface 14F extending the length of the post 14. A set screw 22 is threaded into the locking plate. The inner end of the set screw bears on the flat 14F on the post to lock the plate to the post after fixation of the plates to the spinal processes by a compression instrument. Various spinal compression tools available on the market may be used. Part-spherical recesses 26 (FIG. 6) are provided in the outboard or back face of head plate 12. Similar part-spherical recesses 27 (FIG. 3) are provided in the outboard or back face of the locking plate. These recesses facilitate placement of tips of a compression tool and retention of the tool onto the plates during compression of the plates onto the spinal processes.

Figure 7:
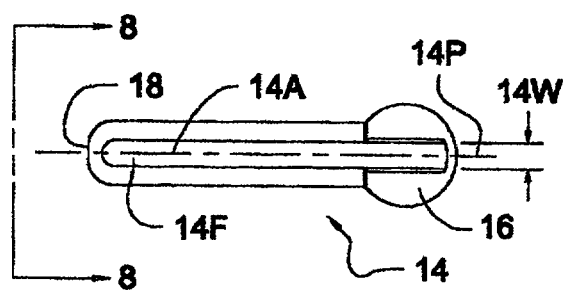
FIG. 7 is a view of the cross-post.
Figure 8:
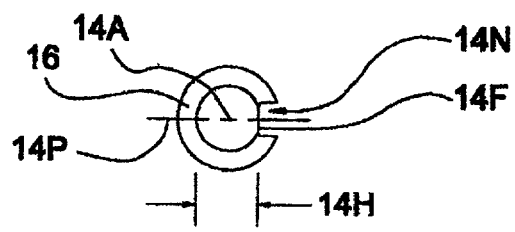
FIG. 8 is an end view of the cross-post taken at line 8—8 in FIG. 7 and viewed in the direction of the arrows.

Referring now to FIGS. 7 and 8, the cross-post 14 is cylindrical, has a spherical head 16 at one end, and the distal end 18 is rounded. While the flat 14F subtends a very narrow arc of the cylindrical surface of the post, it provides a relatively deep groove or notch 14N in the head 16. As an example, where the post head is 7.14 mm in diameter, and the post diameter is 4.49 mm, the dimension 14H (FIG. 8) on a diametrical line in plane 14P bisecting the flat and groove 14N is 4.29 mm, and the width 14W (FIG. 7) of the slot, groove or notch 14N in the post head is 2.353 mm.

Figure 11:
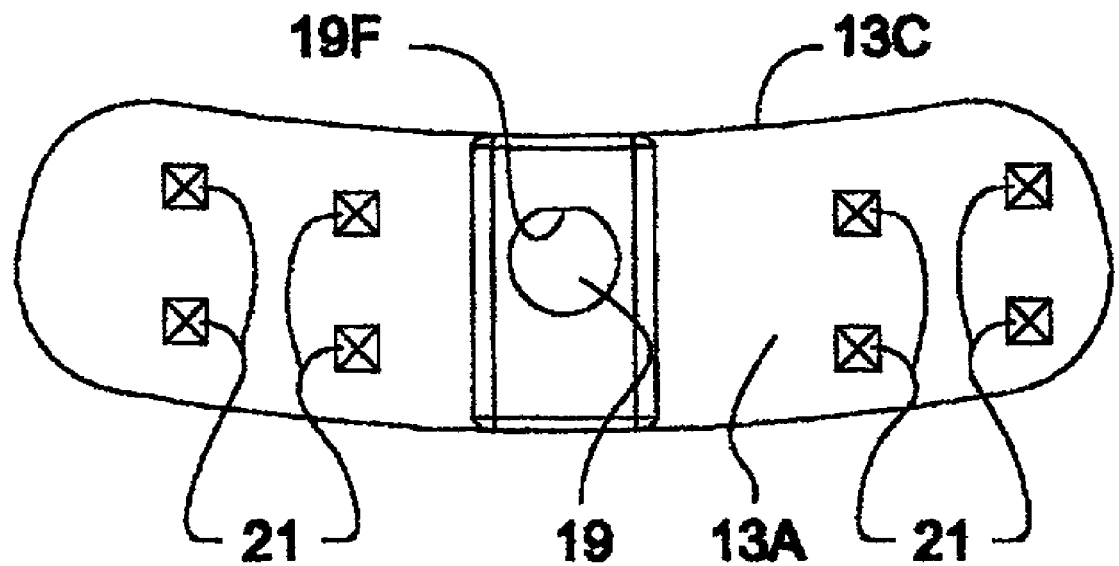
FIG. 11 is a view of the inner face of the locking plate viewed in the direction of the axis of the cross-post receiving aperture.

FIG. 11 is a view of the inboard face 13A of the locking plate, viewed along the axis of the aperture 19. A flat 19F is shown at the top of the aperture. This aperture 19 is thus shaped to provide a sliding, non-rotating fit between the plate and the cross-post. The flats on the post and in the hole 19 are interruptions in the circular form of the post and hole. The post and hole could be of some other cross sectional shape providing a slip fit but avoiding rotation of the locking plate relative to the post. For example, polygonal or key and keyway shapes could be used.

Figure 4:
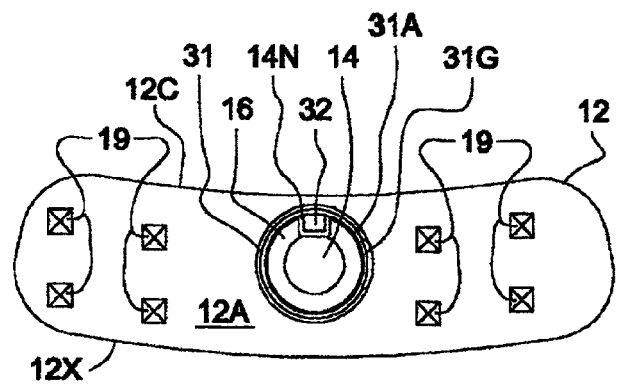
FIG. 4 is a view of the inner face of the head plate with the cross-post secured in a socket therein and the assembly viewed along the longitudinal axis of the cross-post.
Figure 6:
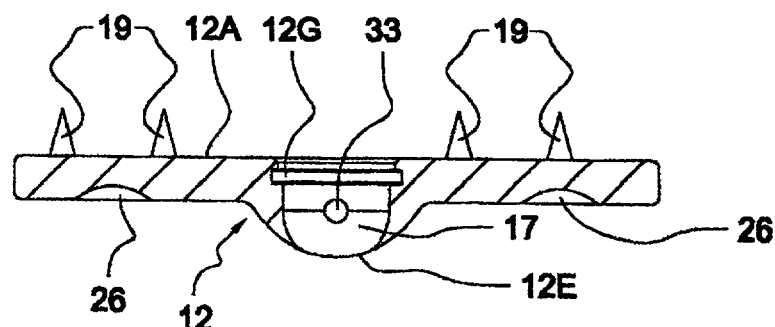
FIG. 6 is a section through the head plate itself taken at line 6—6 in FIG. 5 and viewed in the direction of the arrows.

Referring back to FIG. 4, along with FIGS. 6 and 9, the head plate 12 is viewed facing the inboard surface 12A and looking along the axis 14A of the cross-post 14. The post head 16 is shown received in the socket 17. A snap ring 31 is received in a groove 12G (FIG. 6) at the entrance to the socket 17 and retains the post head 16 in the socket. It was mentioned above that the matching surfaces of the cross-post and the post receiving hole 19 in the locking plate prevent rotation of the plate relative to the post. At the head plate end of the cross-post, a cylindrical pin 32 press-fitted in a hole 33 (FIGS. 6 and 9) in the head plate, projects into the groove 14N of the cross-post head. As shown in FIG. 4, a narrow space is allowed between each side of the groove and the wall of the pin 32. This permits a very narrow angle (maximum five degrees total) of rotation of the head plate relative to the cross-post about the cross-post axis 14A.

At the opposite end of the cross-post, a blind hole 13B extends from the top edge of the locking plate through the aperture 19 in the plate. The upper portion of the hole 13B is of greater diameter and tapped with internal threads to receive the external threads 22T of set screw 22. The screw is shown in FIG. 9 as tightly engaging the flat surface 14F of the cross-post. As shown in FIGS. 3 and 9, the set screw has an upper or outboard head portion 22U with flutes 22F exposed at the upper end of the screw to receive a screw installation tool. There is also a set of flutes 22K (FIG. 9) at the inboard end of the set screw. Each of the two sets of flutes can accommodate a six fluted tool but, of course, of different diameters. At the lower end of the necked-down portion 22N of the set screw, there is an annular notch 22B whereby, following installation and adequate tightening of the set screw, the head can be broken off from the threaded portion to minimize bulk at the outboard edge 13C of plate 13.

Referring further to FIG. 9, it should be understood that in the preferred embodiment, the radius of the spherical portion of the socket is the same as the radius of the spherical head on the cross post. In FIG. 9 there appears to be a space between the socket and the post head at the top. This is because of the cut in the post head providing the slot 14N.

It should also be noted in FIG. 9 that the snap ring 31 has two chamfers 31A and 31B at the hole through it and extending inward from each face of the snap ring. The chamfers may be flat, but are preferably concave, with a radius the same as that of the post head. In this way, it does not matter which way the snap ring is installed in the groove 12G after the post head is inserted in the socket in the pre-assembly of the device. Also, with the chamfer having a slight concavity of the same radius as the post head, the post head can fittingly seat on the snap ring to resist any tendency of the plates to separate following the installation and compression on the spinous processes, and the locking of plate 13 in place with the set screw.

Figure 5:
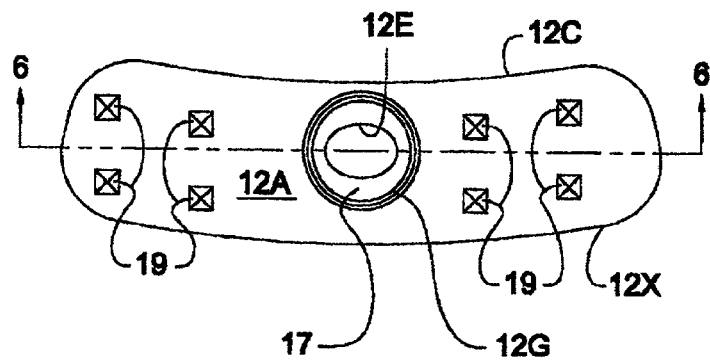
FIG. 5 is a view of the inner face of the head plate without the cross-post, so the post head socket is vacant.

As indicated above, the provision of the socket in the head plate 12, with the post head being swivel mounted in the socket, enables some movement of the plate relative to the axis 14A of the post. The width of the slot 14N, being slightly greater than the diameter of the anti-rotation pin 32, enables a very limited amount (a narrow angle less than five degrees) of rotation of the plate relative to the post about the post axis. Thus, it keeps the plates parallel to each other during insertion of the implant into the patient's back, and during compression of the spikes into the spinal processes, and during clamping of the set screw onto the flat surface 14F of the post. But the head plate also has the capability of angulation relative to the locking plate within an axial (horizontal) plane such as, for example, the plane containing the axis 14A of the post and the axis 32A of pin 32. The plane of the paper for FIG. 9 is an example. Stated in other terms, consider line 6—6 in FIG. 5 to be the longitudinal axis of plate 12. The plate can turn or rotate about this axis up to twenty-five degrees each side of the center of the socket 17, or a total of fifty degrees maximum. The head plate 12 also can angulate relative to locking plate 12 within a coronal (vertical) plane such as, for example, containing the axis 14A of the post and perpendicular to the axis of the pin 32. The plane of the paper for FIGS. 1, 6 and 9, is an example. Stated otherwise, consider a line through the center of the socket 17, such as 32A in plane 9—9, and perpendicular to plane 6—6, and to be the transverse axis of plate 12. The plate 12 can rotate or turn about its transverse axis up to twenty-five degrees each side of the center of the socket.

The device according to the present invention can be used for stabilization following an anterior lumbar interbody fusion procedure. At a suitable time associated with or following the placement of a construct in the interbody site, a small incision is made in the patient's back. The incision is of sufficient size to admit the device and instrumentation. Although angulation of the head plate relative to the post is possible to some extent, rotation of the plate relative to the post is very limited. Neither angulation nor rotation of the locking plate is possible relative to the post. Following the incision, muscle is moved aside if and as needed for placement of the plates. To minimize bulk prior to entry, the two plates can be placed as close together as the surgeon wishes, and the set screw snugged. If the plates have been installed with the spikes thereon touching each other, the set screw can be loosened to spread the plates for mounting on the spinal processes of the vertebrae adjacent the intervertebral construct site. Then the compression instrumentation is applied to press the plates toward each other, whereupon the spikes enter the spinal processes. Compression is continued until the spikes are fully seated. The angulation of the head plate relative to the post is sufficient (up to twenty-five degrees either side of the center line as indicated above), to enable enough adaptation of the plates to different thicknesses and shapes of the spinal processes of adjacent vertebrae, to enable full seating of the spikes in the spinal processes of the adjacent vertebrae. To minimize thickness of the head plate at socket 17, while accommodating post head 16, opening 12E (FIGS. 5 and 6) is provided in the head plate. There is very little clearance between the sphere of the post head and the spherical cavity of the socket, providing a close but slidable fit. The opening 12E enhances effectiveness of autoclave for sanitizing the post head and socket following assembly of the parts outside the patient and before implantation. Although not likely to be needed following the seating of the plates on the spinal processes, the post head end 16E exposed in opening 12E may be lightly pushed toward the snap ring in the direction of arrow 41 (FIG. 9), if needed.

Following the full seating of the plates on the spinal processes, the set screw is tightened onto the flat 14F of the cross-post, using a screwdriver with flutes fitting the outer set of flutes. Upon satisfaction of the surgeon, that the fixation is complete, additional torque is applied to break the head of the set screw away from the threaded portion, and the set screw head is discarded. Then the site is closed up, completing the stabilization procedure. The set screw reliably maintains the clamping force of the plates on the spinous processes. If, at any time, it is decided to remove the device, the inner flutes can receive a smaller fluted head screwdriver to loosen the set screw.

During the compression procedure, and being sure that the post is properly placed, the ability of the head plate 12 to tilt on the post 14 and angulate relative to the locking plate 13, assists in assuring full seating of the spikes on both sides of both spinal processes. The ability of the head plate to tilt relative to the post is limited by engagement of the neck of the head against the inner edge of the snap ring 31. Angulation of the plate relative to the post in any plane is limited by the snap ring edge at about twenty-five degrees each way from the post axis 14A.

The choice of whether the snap ring gap is located as shown in FIG. 4 or on the opposite side of the axis of the post in FIG. 4, or at forty-five degrees up or down from horizontal, may depend upon what the surgeon's impression is of where the strict limitation on angulation should be focused.

While the illustrated example of the device is applied to L-4 and L-5, the device can be implanted on spinous processes at other levels. Levels up to T-3 may be appropriate sites. Also, plates bridging more than one level may also be considered. The shape of the plates may be different at different levels. The virtually identical perimeter edge concavo/convex shape and size of the illustrated plates 12 and 13, conforms generally to the lordotic curve in the lumbar region. In this example, the concave edge 12C and convex edge 12X have a common center remote from the plates and in the plane of the face 12A of the plate. This common center is on a transverse axis of the plate such as mentioned above and which lies on a radius of the center of socket 17 to the common center of curvature of edges 12C and 12X. Plate faces other than flat may be used. Edge shapes other than the banana-shaped profile shown, may be used. Various bio-compatible materials can be used. Titanium-6A-4V ASTM F-136 is an example of plate, pin, post, lock ring, and screw material. Other materials may be used.

The fact that the entire device can be assembled outside the body prior to implantation, but without excessive bulk inhibiting implantation, can be quite helpful in avoiding a multi-component device requiring assembly inside the body. The integral approach reduces the size of the incision required for implantation. Even though the device is pre-assembled, it provides for the plates to angulate relative to each other in two planes, allowing the device to adapt to variations in spinous process thickness and geometry. Use of the integral spikes, rather than screws or shapes which require notching or other treatment of the spinous processes, simplifies the stabilization of the spinous processes following the ALIF. The incorporation of the cross-post in a secure way in the one plate, avoids the need for the use of separate bolt and cable to join plates.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An implantable device for fixation of spinous processes and comprising:
   first and second spaced plates, said first plate having a surface facing a surface of said second plate;
   a post connected to each of said plates and extending from said facing surface of said first plate to said facing surface of said second plate;
   the connection of said post to said first plate being pivotable to enable changing the attitude of said first plate relative to said second plate; and
   the connection of said post to said second plate being adjustable to enable changing the spacing between said first plate and said second plate.

2. The device of claim 1 and wherein:
   said second plate has an aperture therein,
   a portion of said post is slidably received in said aperture; and
   a set screw is received in said second plate and engaged with said post to fix the post to said second plate.

3. The device of claim 2 and wherein:
   said post portion and said aperture have interfitting surfaces shaped for preventing rotation of said second plate relative to said post.

4. The device of claim 3 and wherein:
   the interfitting surfaces are a flat surface on said post and a flat surface in said aperture.

5. The device of claim 1 and wherein:
   said second plate has an aperture therein;
   said post has a portion slidably received in said aperture; and
   said slidably received post portion is non-rotatably received in said aperture, to prevent rotation of said second plate relative to said post.

6. The device of claim 5 and wherein:
   said slidably received post portion is elongate, has a generally cylindrical external surface with a longitudinally extending interruption in the cylindrical shape; and said aperture has a generally cylindrical bore with an axially extending interruption fitting the interruption on the post portion and preventing rotation of the second plate on the post.

7. The device of claim 6 and further comprising:
means on said second plate for locking said post to said second plate to fix a selected spacing between said plates.

8. The device of claim 7 and wherein said means for locking include:
a set screw threaded into said second plate and engageable with a flat surface of said post portion sufficiently tightly to prevent sliding of said post portion in said second plate.

9. The device of claim 5 and wherein:
said post portion is elongate, has a solid generally circular cross-sectional shape but omitting a segment of the circle and;
said device has means for preventing rotation and which include a flat surface extending longitudinally on said post portion at the omitted segment of the circle and fittingly engaging a flat surface of said aperture.

10. The device of claim 1 and wherein:
said facing surfaces have arrays of spikes projecting from said surfaces to penetrate spinous processes in space between said plates to achieve fixation to spinous processes between said plates.

11. The device of claim 10 and wherein:
said facing surfaces are flat.

12. The device of claim 1 and wherein:
the first plate has a socket with a center;
said post has a longitudinal axis and a head received in said socket and pivotable in said socket whereby said post is pivotable relative to said facing surface of said first plate, in two planes perpendicular to each other;
said post has a groove in said head; and
said first plate has a guide pin projecting into said socket and received in said groove for inhibiting rotation of said first plate relative to said post in a plane perpendicular to the axis of said post.

13. The device of claim 12 and wherein:
said post has said head at one end and a guide surface extending from said head toward an other end of said post;
said second plate has an aperture receiving said post through the aperture; and
the aperture has a guide-following surface engaging the guide surface on said post to inhibit rotation of said second plate relative to said post in a plane perpendicular to the axis of the post.

14. The device of claim 13 and wherein:
the guide surface is flat; and
the aperture in said second plate is intercepted by a set screw tightened into said second plate and having an end engaging said flat guide surface and preventing translation of said second plate along said post and preventing rotation of said second plate relative to said post.

15. The device of claim 13 and wherein:
said second plate is elongate, having a longitudinal axis lying in a first plane of said two planes, and said second plate having a transverse axis lying in a second plane of said two planes;
said second plane is perpendicular to said first plane; and
said first plate is elongate, having a longitudinal axis lying in and pivotable in said first plane, and said first plate having a transverse axis lying in and pivotable in said second plane.

16. The device of claim 15 and further comprising:
a retaining ring in said socket and sized and located to engage said post upon pivoting said first plate in said first plane and in said second plane to limit maximum angulation of said axes of said first plate in said first and second planes to less than twenty-five degrees from the center of the socket.

17. The device of claim 16 and wherein:
said first plate and said second plate are arrayed in generally parallel spaced relationship, with said post spanning the space between said plates;
said first plate has a surface facing a surface of said second plate; and
said facing surfaces have arrays of spikes projecting from said surfaces to penetrate spinous processes in space between said plates.

18. The device of claim 17 and wherein:
said facing surfaces are flat.

19. The device of claim 18 and wherein:
said plates have a banana-shaped profile.

20. The device of claim 19 and wherein:
the transverse axis of said second plate is co-linear with radii of concave and convex concentric edges of said plate which are in concentric circles about a center in space remote from said second plate, whereby said edges define a concavo convex shape of said second plate in the plane of said facing surface thereof.

21. The device of claim 20 and further comprising:
a set screw which projects from said concave edge toward said center.

22. The device of claim 21 and wherein:
said set screw has a tool receiver head thereon.

23. The device of claim 22 and wherein;
said set screw has a first threaded portion beginning at said engaging end and having a first tool receiver opening therein facing in a direction away from said concave edge toward the center;
said set screw head has a second tool receiver opening facing away from said concave edge toward said center; and
said set screw has a portion of reduced thickness for facilitating the break-away of the head from the threaded portion following installation at a treatment site.

24. The device of claim 1 and wherein:
said first plate has a socket;
said socket opens in said facing surface of said first plate;
said post has a head received in said socket and said post projects out of said facing surface of said first plate and is pivotable in said socket whereby said post is pivotable in two planes relative to said first plate;
said first plate has a back surface with a socket access opening therein; and
a portion of said post head is exposed in said opening.

25. The device of claim 24 and further comprising:
a retainer ring in said socket retaining said head in said socket.

26. A method of fixation of spinous processes of a subject comprising:
assembling components into an implant assembly comprising first and second plates with a post having one end pivotally mounted in a socket in a first plate and the post having an opposite end slidably received in the second plate;

making an incision in the subject;

inserting the assembly to position adjacent the spinous processes;

sliding the second plate on the post and thereby providing space between the first and second plates to receive spinous processes between the first and second plates;

compressing the plates onto spinous processes; and holding the plates compressed against the spinous processes and clamping said second plate onto the post with a set screw.

27. The method of claim 26 and further comprising:

angulating the first plate relative to the second plate in at least one plane during compression of said plates on said spinous processes.

28. The method of claim 27 and further comprising:

angulating the first plate relative to the second plate in two planes during compression of said plates onto said spinous processes.

29. The method of claim 28 and further comprising:

pressing spikes on said plates into the spinous processes during compression of the plates against the spinous processes.

30. The method of claim 28 and wherein:

angulation of the first plate relative to the second plate is in coronal and axial planes.

31. The method of claim 26 and further comprising, prior to inserting the assembly to position adjacent the spinous processes:

closing the second plate onto the first plate;

locking the second plate closed with a set screw clamping the second plate onto the post;

making an incision in the back of the subject;

then inserting the assembly to position adjacent the spinous processes;

inserting a screw driver and unlocking the set screw;

sliding the second plate on the post and thereby increasing the spacing between said plates;

moving to desired positions adjacent the spinous processes to be fixated; and then compressing the plates against said spinous processes.

32. The method of claim 31 and further comprising:

engaging spikes of facing surfaces of said plates with said spinous processes; and forcing the spikes into the engaged spinous processes during compressing the plates onto the spinous processes.

33. The method of claim 32 and further comprising:

using a screw driver to lock the second plate on the post while compressing the spikes into the engaged spinous processes.

34. The method of claim 33 and further comprising:

breaking the head off the set screw; and closing the incision.

* * * * *